(12) United States Patent
Conerly et al.

(10) Patent No.: US 7,070,773 B2
(45) Date of Patent: Jul. 4, 2006

(54) CHEMICAL AND/OR BIOLOGICAL DECONTAMINATION SYSTEM

(75) Inventors: Lisa L. Conerly, Quincy, MA (US);
Daniel J. Ehntholt, Hudson, MA (US);
Alan S. Louie, Sudbury, MA (US);
Richard H. Whelan, Norfolk, MA (US)

(73) Assignee: Tiax LLC, Cambridge, MA (US)

( * ) Notice: Subject to any disclaimer, the term of this patent is extended or adjusted under 35 U.S.C. 154(b) by 117 days.

(21) Appl. No.: 10/182,821

(22) PCT Filed: Feb. 1, 2001

(86) PCT No.: PCT/US01/40011

§ 371 (c)(1),
(2), (4) Date: Jul. 31, 2002

(87) PCT Pub. No.: WO01/56380

PCT Pub. Date: Aug. 9, 2001

(65) Prior Publication Data

US 2003/0109017 A1    Jun. 12, 2003

Related U.S. Application Data

(60) Provisional application No. 60/179,499, filed on Feb. 1, 2000.

(51) Int. Cl.
*A61K 38/43*   (2006.01)
*A61K 38/46*   (2006.01)
*A61K 33/32*   (2006.01)
*A01N 25/00*   (2006.01)

(52) U.S. Cl. .................... 424/94.1; 424/94.6; 424/405; 424/639

(58) Field of Classification Search ............... 424/94.1, 424/94.6, 405, 639
See application file for complete search history.

(56) References Cited

U.S. PATENT DOCUMENTS

| | | | | |
|---|---|---|---|---|
| 5,348,738 | A | * | 9/1994 | Takatsuka et al. ....... 424/78.37 |
| 5,626,838 | A | * | 5/1997 | Cavanaugh, Jr. ............. 424/54 |
| 5,696,069 | A | * | 12/1997 | Ito et al. ..................... 510/123 |
| 5,874,476 | A | * | 2/1999 | Hsu et al. ................... 514/640 |
| 5,891,422 | A | * | 4/1999 | Pan et al. ..................... 424/49 |

OTHER PUBLICATIONS

Grice et al. Agric. Food Chem. 1996. vol. 44, pp. 351-357.*
Smith et al. Biotechnol. Bioengineering. 1992. vol. 39, No. 7, pp. 741-752.*

* cited by examiner

*Primary Examiner*—Christopher R. Tate
(74) *Attorney, Agent, or Firm*—Lowrie, Lando & Anastasi, LLP

(57) ABSTRACT

The present invention provides compositions effective in decontaminating either biological pathogens or both chemical and biological pathogens. These compositions are particularly suitable for the decontamination of biological warfare agents or both chemical and biological warfare agents The compositions comprise generally a blend of biocides, and may additionally comprise a protein and an enzyme. Further, the composition is contained in a buffered foam forming material for ease in distribution The compositions are nontoxic, noncorrosive and nonflammable.

8 Claims, No Drawings

CHEMICAL AND/OR BIOLOGICAL DECONTAMINATION SYSTEM

The present application claims the benefit of U.S. provisional application No. 60/179,499, filed on Feb. 1, 2000, the teaching of which is incorporated herein by reference.

STATEMENT OF GOVERNMENT INTEREST

Funding for the present invention was obtained from the Government of the United States by virtue of Contract No. DAAD05-98-C-0005 from the U.S. Department of the Army. Thus, the Government of the United States has certain rights in and to the invention claimed herein.

FIELD OF THE INVENTION

The present invention relates to noncorrosive, nonflammable and nontoxic compositions effective in decontaminating biological pathogens, and combinations of both toxic chemical agents and biological pathogens. These compositions are useful in a variety of applications where toxic chemical or biological contamination may be of concern. The present compositions are particularly suitable for the decontamination of biological warfare agents and combinations of both chemical and biological warfare agents. The compositions are particularly effective in decontaminating the nerve gas Sarin (GB) and the biological warfare agent Anthrax. More particularly, the compositions of the present invention comprise at least one biocide, preferably a blend of biocides, and may additionally comprise a chemical agent binding protein and an enzyme which is active against organophosphorous compounds. The compositions preferably further include a foam forming material.

BACKGROUND OF THE INVENTION

The possible use of chemical and/or biological warfare agents during a military action or terrorist attack presents a continuous threat to U.S. military and civilian personnel. The advances in the biotechnology area and the resulting ease of preparing significant quantities of infectious agents and biological toxins have further increased the chemical and biological warfare threat.

Anthrax has been identified as one of the most probable biological warfare agent terrorist threats. Typically, anthrax would be disseminated as an aerosol in a terrorist act. The mortality rate of exposed, untreated individuals is greater than 90% and would be expected to act in 1 to 7 days, with most deaths occurring within 48 hours. Anthrax spores are extremely hardy and can persist in the environment for more than 50 years. Many biological warfare agent decontaminants are not effective against anthrax spores.

In the event of an attack in which chemical and/or biological warfare agents are used, U.S. military personnel or civilian first responders may be directly exposed to such agents as they enter contaminated areas. There are several decontaminants currently available. However, these decontaminants are generally themselves hazardous materials to handle and dispose of and may not be effective against some agents. Further, the present decontaminants are stable for only very limited time periods. Still further, the present decontaminants are typically effective against only chemical or biological agents, but not both. Thus, protection of vulnerable populations requires storage and deployment of different types of protective agents to safeguard these populations against different attacks.

Recently, in addition to typical biological warfare agents, a further threat is the use of any microorganisms or toxins derived from microorganisms which cause disease in man, plants, or animals. Prior decontaminants are designed specifically for use against biological warfare agents and are not suitable for use against the many other types of pathogens that may be used.

There is a need for nonhazardous compositions that are effective in decomposing chemical and biological warfare agents. There is a further need for compositions that remain stable for extended periods of time and are easily applied to large surface areas. Additionally, there is a need for a single composition that is effective against both chemical and biological warfare agents. Still further, there is a need for a composition that is effective against all types of pathogens, not only biological warfare agents.

SUMMARY OF THE INVENTION

The present invention provides compositions effective in decontaminating biological pathogens and compositions effective in decontaminating combinations of chemical agents and biological pathogens. As used herein, the term "biological pathogen" includes any microorganism, or a toxin derived from a microorganism which causes disease in man, plants, or animals, and includes biological warfare agents. As used herein, the term "chemical agent" includes chemical substances which are intended for use to kill, seriously injure, or incapacitate people through their physiological effects.

The compositions of the present invention are useful in a variety of applications where toxic chemical or biological contamination may be of concern. These compositions are particularly suitable for use against biological warfare agents and combined chemical and biological warfare agents.

The biological pathogen decontaminant composition of the present invention comprises at least one biocide component. Preferably, the biological pathogen decontaminant composition comprises a blend of biocides The combined chemical and biological pathogen decontaminant compositions of the present invention are chemically compatible and comprise generally at least one biocide component, a chemical agent binding protein and an enzyme active against organophosphorous chemical agents. These compositions preferably further include a buffered solution or foam forming material for ease in application to large surface areas.

The biocide component preferably comprises a known biocide, or, more preferably, a blend of known biocides, which is effective against bacteria and other microorganisms present in biological pathogens. For example, useful biocides may include triclosan, tetrakishydroxymethyl phosphonium sulfate (THPS), benzalkonium chloride (BAC) and streptomycin. Triclosan is a broad spectrum antibacterial chemical used in a variety of commercial products. THPS is a broad spectrum EPA approved biocide used in a number of industrial processes. BAC is a broad spectrum biocide used in commercial disinfectants. Streptomycin is an antibiotic that is based on its ability to inhibit protein synthesis. In a particularly preferred embodiment, the biocide blend comprises combinations of triclosan, THPS and BAC.

The binding proteins function to bind and preferably denature or otherwise disable the chemical agents, and may be selected from those known in the art. For example, some suitable proteins may include albumin, e.g. bovine serum albumin (BSA), acetylcholinesterase (AChE), butyl cholinesterase (BuChE), cholinesterase (ChE), chymotrypsin, trypsin, chymotrypsinogen, trypsinogen, urokinase, esterase, carboxylesterase, thrombin, Factor VII$_A$, Factor X$_A$, kallikrein, prekallkrein, Na/K-ATPase, papain and alkaline phosphatase. Preferably, the protein is bovine serum albumin.

Preferably, enzymes, which are active against organophosphorous species, are further added. Such enzymes are known, and may include, for example, glucose oxidase, lysing enzyme, lysozyme, protease, chitinase, lysostaphin, mutanolysin, collagenase, SynthaCLEC-GO (Altus, Inc., Cambridge, Mass.) and PeptiCLEC-TR (Altus, Inc., Cambridge, Mass.). Chitinase is an enzyme that hydrolyses N-acetal-D-glucosamine from cell walls. Lysozyme is an enzyme that hydrolyses cell wall components (β-1,4-glucosidic linkages). Mutanolysin is Gram positive specific enzyme that hydrolyses cell wall components. In addition, organophosphate hydrolase (OPH) or organophosphorous acid anhydrase (OPAA) are enzymes capable of detoxifying organophosphorous neurotoxins. Preferably, OPAA or OPH is used, with OPAA being particularly preferred.

As a foam forming material, any known fire-fighting foam may be used, including, for example, Silv-Ex™ foam (Ansul Incorporated, Marinette, Wis.), Aqueous Film-Forming Foam (AFFF), and Film-Forming Fluoroprotein (FFFP). Other foam materials may also be used including, for example, solid foams such as polyurethanes and sponges. The present composition is preferably contained in Silv-Ex™ fire-fighting foam, which does not interfere with the binding functions of the proteins, the enzymatic activity against chemical agents or the activity of the biocide(s) against biological pathogens, including cells, spores, viruses, and parasites.

The present composition is preferably maintained at suitable pH levels for optimal decontamination. Preferably, the composition is maintained at a pH level ranging from about 6.0 to about 8.5. Any suitable known buffers, including, for example, phosphate, carbonate, Tris, MES, PIPES, ACES, MOPS, TES, HEPES, HEPPS, TRICINE, and Glycine buffers may be added for this purpose. Preferably, a phosphate buffer is used.

In addition to the above components, trace metals such as, for example, $MnCl_2$, $MgCl_2$, $CaCl_2$, $CdCl_2$, $CoCl_2$, $CuCl_2$, or $FeCl_2$, may be added to enhance the enzyme activity. A particularly preferred trace metal is manganese chloride.

The composition is preferably stored in two separate containers for added stability prior to use of the composition. Preferably, one container contains the biocide mixture A foam forming material is preferably further added to this container. This mixture of biocide and foam forming material has at least a 12 month shelf life at ambient temperature. The second container preferably contains the enzyme and protein components. The contents of the second container are stable for at least 6 months at temperatures in the range of 2–4° C. The contents of the two containers may be mixed for combined decontamination of both chemical agents and biological pathogens, or, if desired, the contents of the biocide container may be used alone. Upon mixing of the two containers to obtain the composition of the present invention, the mixture will remain stable for at least 24 hours at ambient temperature Other aspects of the invention are discussed infra.

DETAILED DESCRIPTION OF THE INVENTION

The present invention provides a composition that is effective in the decontamination of chemical agents and/or biological pathogens. The biological pathogen decontaminant composition of the present invention comprises a biocide component. The combined chemical and biological pathogen decontaminant compositions of the present invention are chemically compatible and comprise generally a biocide component, a protein and an enzyme. The compositions may further comprise a foam forming material.

The compositions of the present invention may be used in the decontamination of such chemical agents and biological pathogens including: GA, GB, GD, GF, VX, and mustard gas, and Anthrax, the plague, tularemia, cholera, E. coli 0157:H7, and Shigella, respectively. In particular, the present composition is effective in decontaminating the nerve gas Sarin (GB) and the biological warfare agent Anthrax.

The chemical agent decontaminant of the present invention comprise at least one enzyme and protein.

A variety of enzymes may be used, including, for example, glucose oxidase, lysing enzyme, lysozyme, protease, chitinase, lysostaphin, mutanolysin, collagenase, SynthaCLEC-GO and PeptiCLEC-TR In addition, organophosphate hydrolase (OPH) and preparations of organophosphorous acid anhydrase (OPAA), enzymes known to be active against organophosphorous species (See, for example, DeFrank and Cheng, *Purification and Properties of an Organophosphorous Acid Anhydrase from a Halophilic Bacterial Isolate*, Journal of Bacteriology, pp. 1938–1943 (March 1991)), maybe used.

These enzymes are available in different forms, including specific forms that provide for added stability in harsh environments. For example, enzymes may be in the form of crosslinked enzyme crystals (CLEC), which contain crystallized enzyme matrices that have been crosslinked to maintain physical structure and enzyme configuration and activity. Such enzymes may possess enhanced stability, both in storage and in an active matrix, as well as resistance to digestion by other enzymes.

Preferably, the enzyme is an enzyme active against organophosphorous chemical agents.

The chemical agent decontaminant further comprises proteins which, without being bound by theory, are believed to bind to chemical agents. These binding proteins may be selected from those known in the art, including, for example, any of the following: albumin, e.g. BSA, AChE, BuChE, ChE, chymotrypsin, trypsin, chymotrypsinogen, collagenase, trypsinogen, urokinase, esterase, carboxylesterases, thrombin, Factor VII$_A$, Factor X$_A$, kallikrein, prekallikrein, Na/K-ATPase, papain and alkaline phosphatase.

These proteins preferably do not interfere with the activity of the enzymes and biocides in the composition. Thus, during the testing of potential proteins, it is important to analyze not only which binding proteins were effective in binding to chemical agents, but also to note which proteins do not interfere with the activity of the enzymes and biocides in the composition. Some preferred binding proteins include albumins, particularly BSA.

Sarin (GB) is a well-recognized organophosphorous-based chemical warfare agent. Diisopropyl fluorophosphate (DFP) is an organophosphorous compound that is less toxic and possesses chemical properties closely related to Sarin. Many materials with activity against DFP will also possess activity against other G agents, such as VX, in addition to Sarin. Thus, in analyzing enzymes, DFP is often used during testing as a surrogate for Sarin.

The overall strategy for decontamination of chemical agents follows two directions: (1) Quantitative decontamination—direct competitive inhibition of agent binding to acetylcholinesterase (AChE) and (2) Catalytic decontamination—deactivation and digestion of the agent by digestive enzymes. Quantitative decontamination prevents the action of chemical agents on humans, while catalytic decontamination results in extended activity and catalytic decontamination over time.

During the quantitative decontamination procedures, materials were evaluated for their direct impact on the chemical warfare surrogate, DFP, using the Ellman's assay, (See Ellman, G. L., Courtney, D., Andres, Jr., V., and Featherstone, R. M., *A New and Rapid Colorimetric Determination of Acetylcholinesterase Activity*, Biochemical Pharmacology, Vol. 7, pp. 88–95 (1960)), to determine their ability to inhibit DFP.

During initial studies, potential foam forming materials, biocides and proteins were tested to see if any of these components would provide additional inhibition of chemical agents. These studies demonstrated that Silv-Ex™, triclosan, THPS, and BAC do not inhibit the chemical agent DFP, while the binding protein bovine serum albumin (BSA) provides additional DFP inhibition.

Following initial studies, OPH, preparations of OPAA, and collagenase enzymes were evaluated for their direct inhibition of DFP. Additionally, BSA, a potential binding protein for use in the composition, and FFFP foam, a potential foam forming material for use in the composition, were analyzed to determine if either material added to DFP inhibition. Based on its fluoroprotein compositions, it is believed that FFFP foam, like BSA could provide a similar protective activity as demonstrated by the BSA in the initial studies. The test results, as set out in Example 3, demonstrate that OPH and OPAA are both capable of significantly inhibiting DFP. Collagenase only moderately inhibited DFP at concentrations of 3 mg/mL or higher. Further, while FFFP foam showed no effect against DFP, BSA showed some DFP inhibition. Additional DFP inhibition was not demonstrated for the other materials tested. Active materials would be expected to produce a protective effect in preventing DFP from inhibiting the AChE present in the Ellman's assay. BSA was identified as capable of quantitative binding to G-type agents. In conjunction with enzymatic approaches to decontamination, BSA is expected to perform a number of functions, including elimination of residual chemical agents by direct binding, stabilization of other protein components, and prevention of enzyme loss by surface neutralization.

Of particular concern in the use of enzyme-based approaches is efficacy, stability both in storage and in an active matrix, compatibility with other decontaminants, and cost. Further, in the development of multi-enzyme based decontaminant systems, a problem exists with the possibility for interaction between the active enzyme materials, resulting in self-inactivation. Thus, a number of potential enzymes were analyzed in Example 4, to determine the impact of these enzymes on acetylcholinesterase (AChE) As shown, glucose oxidase, lysing enzyme, lysozyme, protease and synthaCLEC-GO all demonstrated a significant impact on the Ellman's assay in terms of reduction in AChE enzyme activity. Chitinase, lysostaphin and mutanolysin also demonstrated interference with the AchE enzyme.

Another concern in the development of a multi-component chemical and biological pathogen decontaminant foam is the potential impact (either positive or negative) of the foam forming material on enzyme activity. In Example 5, the enzymes were tested for interference by Silv-Ex™ foam. It was demonstrated that Silv-Ex™ can potentially interfere with the activity of some enzymes, although results suggest that the interference occurs mostly through reduction in available enzyme activity through precipitation of the enzyme. While full activity was retained for chitinase, lysing enzyme and mutanolysin, only partial activity was observed for glucose oxidase, lysozyme, protease and synthaCLEC-GO.

Throughout the testing of various enzymes, preparations of OPAA and OPH both showed favorable results for use as decontaminant enzymes. However, it was found that the biological pathogen decontaminant biocides interfered with the OPH activity. Thus, the OPAA preparations are preferred enzymes for use in biological and chemical agent decontaminant compositions containing biocide components. Further, due to technical advances in OPAA enzyme expression, OPAA may be a particularly preferred enzyme for use in the present composition.

The enzyme utilized is preferably present in a single strength composition at about 0.1 to about 350 mg/L. Preferably, the enzyme is present from about 1.6 to 70 mg/L. Most preferably, the utilized enzyme is present at about 3.3 to 12 mg/L. As used herein, mg/L is intended to refer to milligrams of enzyme per Liter of single strength foam solution. Preferably, the binding protein is added to the present composition at levels of from about 0.001 to about 40 g/L, more preferably from about 0.005 to 10 g/L, and more preferably from about 0.01 to 1.0 g/L. As used herein, g/L is intended to refer to grams of binding protein per Liter of single strength foam forming material.

The biological pathogen decontaminant composition of the present invention comprises at least one biocide and, more preferably, comprises a blend of biocides. A number of chemical biocides are currently in wide use to eliminate bacteria in commercial applications including, for example, benzalkonium chloride (BAC), tetrakishydroxymethyl phosphonium sulfate (THPS), {phosphonium, tetrakis(hydroxymethyl)-, sulfate)}, triclosan {2,4,4'-trichloro-2'-hydroxydiphenyl ether}, streptomycin, Sodium omadine®, Dichlorophen and methylene bisthiocyanate. Any of these biocides may be used in the biological pathogen decontaminant composition. Commercial biocides offer a number of advantages, including broad spectrum efficacy against several classes of bacteria, activity at ppm levels, and prior manufacturer registration for use with the FDA or EPA or both.

In the biological pathogen decontaminant development, the experimental studies were focused on testing surrogates to both Anthrax spores and vegetative cells. While recognizing that spores are the primary weaponized-form of Anthrax, evaluation of vegetative cells were investigated in order to provide additional insights into bacillus susceptibility. Initial efforts in the development of both the detection and decontaminant options against Anthrax used *Bacillus globigii* as a surrogate to Anthrax. This surrogate bacterium is non-pathogenic and forms spores physically similar to *Bacillus anthracis* (Anthrax). Additionally, other appropriate biological surrogates to Anthrax were also tested to increase efficacy of the tests. Thus, the tests were expanded to include a number of bacillus species most closely related to anthrax. Researchers in the field generally agree that the two bacillus species most closely related to anthrax are *Bacillus cereus* and *Bacillus thuringiensis. Bacillus cereus* is an opportunistic human pathogen, requiring careful handling. *Bacillus thuringiensis* is non-pathogenic in humans, but is widely used for its biopesticide activity against insects. Thus, during biological pathogen decontaminant development, six different bacillus organisms, which behave as either physical or biological surrogates to anthrax, were evaluated in parallel:

Bacillus cereus (ATCC 11950)
Bacillus cereus (ATCC 49063)
Bacillus cereus (ATCC 49064)
Bacillus globigii (ATCC 51189)
Bacillus subtilis var. niger (ATCC 9372)
Bacillus thuringiensis (ATCC 29730)

The overall strategy for decontamination of chemical agents, described above, was also considered for decontamination of biological pathogens. Direct inactivation of vegetative cells or spores would be expected to prevent infection of biological pathogens in humans (i.e., quantitative decontamination). Alternatively, digestion of biological pathogens by specific enzymes could also eliminate this threat (i.e., catalytic decontamination). It would be expected that enzymes used to decontaminate chemical agents may also demonstrate activity against natural toxins and other biological pathogens. Thus, in addition to biocides, a number of enzymes including, for example, chitinase, lysozyme and mutanolysin may also demonstrate potential activity against biological pathogens.

Preliminary studies were performed to determine the potential impact of various biocides, enzymes and proteins on the Ellman's assay. The studies demonstrated that triclosan, EDTA, urea, bovine serum albumin (BSA), Silv-Ex™, Aqueous Film Forming Foam (AFFF) and Film-Forming Fluoroprotein (FFFP) foam do not directly impact the assay. In the absence of other biocides, THPS reacts directly with the colorimetric reagent (AChE) used in the Ellman's assay. When blended with other biocides, however, it was found that THPS did not interfere with the Ellman's assay.

Using direct microbiological challenge (i.e. no foam present), the biocides set out above were tested on Bacillus globigii vegetative cells and spores in tryptic soy broth. See Example 6. Throughout the experimental testing, biocides (i.e. THPS, triclosan and BAC) demonstrated the best effects, with complete destruction of all vegetative cells and some destruction of spores. Of the biocides tested, both THPS and triclosan had a bacteriocidal effect on cells and showed no spore germination. BAC was highly bacteriocidal, but showed no effect on spore germination. Studies with mutanolysin against vegetative cells produced a limited and temporary bacteriostatic effect, with growth restored upon dilution of mutanolysin from the media. Studies with supplemented lysozyme appeared to inhibit active spore germination.

While enzyme approaches (particularly supplemented lysozyme) appear promising, direct approaches using biocide blends were preferred, based on increased log-kill of vegetative cells and activity against spores. Thus, blends of triclosan, BAC and THPS in Silv-Ex™ foam were further analyzed. In Example 8, using blends containing triclosan, BAC, THPS and Silv-Ex™ foam, the relative concentrations of the components were varied and tested. This study provided insights into the potential for specific blends of biocides to provide activity against vegetative cells and spores.

In selection of a biocide blend, it was determined that it was possible for a formulation to inhibit growth without destroying the target bacteria. In studies where bacteria were exposed to varying levels of BAC alone, it was demonstrated that BAC possessed bacteriocidal activity at high levels and bacteriostatic activity at lower levels. These initial studies verified the need for continual assessment of bacteriostatic versus bactericidal activity for each biocide formulation.

An intermediate blended biocide composition containing 1.0 wt % Silv-Ex™, 5000 ppm triclosan, 240 ppm BAC and 9,750 ppm THPS, adjusted to a pH of 7.55 was used in direct microbial foam challenges against Bacillus globigii vegetative cells and spores, Bacillus cereus vegetative cells and Bacillus thuringiensis spores. See Example 12.

As tests continued, it was demonstrated that a blended biocide composition containing 1.4 wt % Silv-Ex™ foam, 0.44 wt % triclosan, 250 ppm BAC and 8,800 ppm THPS retained full biocidal activity over a range of pH from 6.0 to 8.5 after 24 hour incubation. Thus, it is preferred that the present composition be maintained at pH levels in the range of about 6.0 to 8.5. To this end, suitable known buffers, such as phosphate, carbonate, Tris, MES, PIPES, ACES, MOPS, TES, HEPES, HEPPS, TRICINE and Glycine buffers may be added. Preferably, a phosphate buffer is used, namely 50 mM sodium phosphate (pH 8.0). The phosphate buffer would be added as required to maintain the pH levels within the desired range of 6.0 to 8.5.

A preferred biocide blend in accordance with the present invention contains up to about 6.6 wt % triclosan, up to about 2.5 wt % BAC and up to about 3.0 wt % THPS. More preferably, the biocide blend contains from about 0.1 wt % to about 1.0 wt % triclosan, from about 0.1 wt % to about 2.5 wt % BAC and from about 0.1 wt % to about 3.0 wt % THPS. Even more preferably, in a single strength composition, the preferred biocide blend contains about 0.5 wt % triclosan, about 0.5 wt % BAC and about 1.5 wt % THPS.

For quick and easy application of the present compositions to a large surface area, the composition is preferably contained in a solution or foam forming material, such as those commonly used. (See, for example, Norman R. Lockwood, *Foam Extinguishing Agents and Systems*, Fire Protection Handbook, 16$^{th}$ Edition, Section 19, Chapter 4, pp. 32–47 (1986)). Such foam forming material may include, for example, Silv-Ex™ foam, Aqueous Film-Forming Foam (AFFF), and Film-Forming Fluoroprotein (FFFP). Other foam materials may also be used such as, for example, solid foams such as polyurethanes and sponges.

The present composition is preferably contained in Silv-Ex™ fire-fighting foam, which demonstrated no negative impact on enzyme or biocide activity. The foam delivery system may be any type used in the field, and is preferably designed to add a single foam concentrate to the hardware delivery system, charge (pressurize) the hardware, and dispense. In some applications, it is further desired that the foam delivery system is designed to add water to dilute to single-strength formulation.

Preferably, the present composition contains about 0.5 to 5 wt % foam forming material. More preferably, the foam forming material is present from about 1.0 to about 3.0 wt %. Even more preferably, the foam forming material is present at about 1.5 to 2.5 wt %. However, the concentration of foam forming material present in the decontaminant composition may be slightly modified without adversely impacting the chemical agent or biological pathogen decontaminant efficacy.

In addition to the above composition, trace metal salts, such as $MnCl_2$, $MgCl_2$, $CaCl_2$, $CdCl_2$, $CoCl_2$, $CuCl_2$, or $FeCl_2$ may be added to enhance the enzyme activity. For example, Manganese, added as Manganese chloride ($MnCl_2$), has been found particularly useful in the present composition utilizing OPAA enzyme. Preferably, trace metal salts are added in amounts from about 0.5 to 2.5 mM. More preferably, trace metal salts are added in amounts from about 0.5 to 1.5 mM.

The preferred chemical agent and biological pathogen decontamination composition of the present invention comprises: (1) a biocide blend—preferably a blend of triclosan, THPS and BAC, (2) a chemical agent binding protein—preferably bovine serum albumin, and (3) an enzyme active against organophosphorous compounds—preferably OPAA. The composition preferably further includes a foam forming material, such as Silv-Ex™, having a buffer, such as a phosphate buffer, for maintaining pH of the composition between about 6.0 and 8.5. Further, trace amounts of metals, preferably manganese in the form of manganese chloride, may be added.

Preferably, a single strength formulation is formulated approximately as follows: up to about 6.6 wt % triclosan, up to about 2.5 wt % BAC, up to about 3.0 wt % THPS, about 0.5 to 2.5 mM manganese chloride, about 1.6 to 70 mg/L OPAA enzyme, about 0.01 to 40 mg/mL bovine serum albumin, about 1 to 200 mM phosphate buffer and about 0.5 to 5 wt % Silv-Ex™.

More preferably, the formulation comprises from about 0.1 wt % to about 10 wt % triclosan, from about 0.1 wt % to about 2.5 wt % BAC, from about 0.1 wt % to about 3.0 wt % THPS, from about 0.5 mM to about 1.5 mM Manganese chloride, from about 3.3 mg/L to about 12 mg/L OPAA enzyme, from about 0.01 mg/mL to about 1.0 mg/mL bovine serum albumin, from about 10 mM to about 100 mM phosphate buffer and from about 1.5 wt % to about 3.0 wt % Silv-Ex™.

A particularly preferred single strength formulation comprises approximately 0.5 wt % triclosan, 0.5 wt % BAC, 1.5 wt % THPS, 1 mM manganese chloride, 7 mg/L OPAA enzyme, 0.1 mg/mL bovine serum albumin, 50 mM sodium phosphate buffer and 2.0 wt % Silv-Ex™.

It has been found that storing the composition in two separate containers prior to use increases stability. Preferably, a mixture of the foam forming material and biocides is stored in one container and a mixture of the enzyme and protein components is stored in the other container. If a buffer is used, it is preferably added to each container. The foam forming material and biocide mixture has at least a 12 month shelf life at ambient temperature. The enzyme and protein mixture may be kept stable for at least 6 months at temperatures in the range of 2–4° C. The two separate containers can be mixed to form a composition capable of decontaminating both chemical agents and biological pathogens. If desired, it is further possible to use the contents of the two containers individually.

Using the above-preferred composition, the two separate containers would preferably contain the following: (1) one container is preferably a 10× foam concentrate containing approximately 5 wt % triclosan, 5 wt % BAC, 15 wt % THPS, 10 mM manganese chloride, 500 mM phosphate buffer (pH 8.0) and 20 wt % Silv-Ex™ and (2) the second container is preferably a 100× concentrate containing approximately 700 mg/L OPAA enzyme, 10 mg/mL bovine serum albumin and 50 mM phosphate buffer (pH 8.0).

To use the composition of the present invention, the contents of the two containers are preferably combined into the foam distribution apparatus Upon mixing of the two containers to obtain the composition of the present invention, the mixture will remain stable for at least 24 hours at ambient temperature. One then simply sprays the foam over a surface, and allows the foam to sit and act on the chemical and/or biological agent. Once a sufficient time has passed to ensure adequate decontamination of the agents, typically at least one hour, the residue is then cleaned up.

The present invention also includes kits that comprise a first mixture, comprising a foam forming material and at least one biocide, and a second mixture, comprising an enzyme active against organophosphorous compounds and a chemical agent binding protein. Kits of the invention also may be include a foam distribution apparatus, preferably packaged with written instructions for use of the compositions and other components of the kit.

The compositions of the present invention will be further illustrated with reference to the following Examples which are intended to aid in the understanding of the present invention, but which are not to be construed as a limitation thereof.

EXAMPLE 1

Foam Generation Procedures

Commercial fire extinguisher units were used as preliminary indicators of foam generation performance. Two small (2 or 2.5 gallon) pressurized fire extinguishers and an Amerex Model 252 aspirating nozzle extinguisher were used. Results of this study were used to determine a preliminary foam surfactant concentration for laboratory studies.

For laboratory generation of foam, a laboratory aerosol spray bottle (Airspray International, 30–100 mL capacity; Nalgene P/N 2430–0200) was used. The spray head from this unit was modified with an 11 gauge thin wall stainless steel delivery tube to enhance foam dispensing.

EXAMPLE 2

Foam Decontamination Efficacy Surface Testing

In evaluating the stability of vegetative cells and spores on glass slides, slides were directly coated with approximately 200 cfu (colony forming units) *Bacillus globigii* (vegetative cells or spores), *Bacillus cereus* (vegetative cells) and *Bacillus thuringiensis* (vegetative cells or spores). The slides were allowed to dry and were periodically swabbed to recover bacteria (Intervals: 10 min, 1 hour, 3 days and 7 days). Viable bacteria were obtained from both vegetative cells and spores for all slides through 7 day storage.

In initial testing of expanded foam decontamination, glass slides were directly coated with *Bacillus globigii* spores and *Bacillus cereus* vegetative cells. Using a hand foam sprayer, a biocide blend preparation containing about 240 ppm BAC and about 5000 ppm triclosan, at a pH of 7.50, was applied to the slide surface. After 10 minutes, the glass surface was swabbed using a sterile cotton swab. Swab samples were then plated to assess bacterial growth. *Bacillus globigii* spores were found to be effectively killed As found with direct broth testing, *Bacillus cereus* vegetative cells were found to be inhibited (i.e., upon dilution of cells into decontaminant-free broth, cells resumed propagation). After a 24 hour incubation with foam, the same slides were re-swabbed, with additional *Bacillus cereus* vegetative cell growth observed.

A study was performed to determine whether a biocide blend decontaminant foam containing about 240 ppm BAC, about 9750 ppm THPS and about 5000 ppm Triclosan, at a pH of 7.55, was effective within the first hour of exposure. Glass slides, as described and prepared above, were sprayed with the biocide mixture. After 1 hour, viable bacteria were recovered from all slides. After 24 hour exposure, *Bacillus globigii* and *Bacillus thuringiensis* were killed (*Bacillus cereus* remained viable, as expected).

Based on these and other results, three promising biocide blend formulations, set out below, were identified for further evaluation. Bacteria-coated glass slides were treated using the laboratory foam generation unit and each of the solutions. This unit and the 2% Silv-Ex™ solutions appeared to be optimal for the development of expanded decontaminant foams. Results indicated that, while bacteria remained active after 10 or 30 minutes exposure, all bacteria (including *Bacillus cereus*) were killed within I hour of exposure using each of the three test compositions.

Composition 1
2.0% Silv-Ex™
0.5% Triclosan
2.5% Benzalkonium Chloride
3.0% THPS
1 mM Magnesium chloride
660 mg/L OPAA enzyme
1.0 mg/mL Bovine serum albumin
in 50 mM Phosphate buffer, pH 8.0

Composition 2
2.0% Silv-Ex™
0.5% Triclosan
05% Benzalkonium Chloride
1.5% THPS
1 mM Magnesium chloride
660 mg/L OPAA enzyme
1.0 mg/mL Bovine serum albumin
in 50 mM Phosphate buffer, pH 8.0

Composition 3
2.0% Silv-Ex™
10% Triclosan
0.5% Benzalkonium Chloride
1 mM Magnesium chloride
660 mg/L OPAA enzyme
1.0 mg/mL Bovine serum albumin
in 50 mM Phosphate buffer, pH 8.0

These compositions are prepared by adding the manganese chloride, OPAA enzyme and bovine serum albumin immediately prior to use. Thus, the compositions were prepared as follows:
1. To 100 mL of prepared solution containing Silv-Ex™, triclosan, benzalkonium chloride, THPS and buffer, add:
   100 μL of manganese chloride (1M)
   66 μL OPAA enzyme (10 mg/mL)
   1 mL Bovine serum albumin (100 mg/mL)
2. Stir at high speed at room temperature for 5 minutes
3. Shake solution well before use
4. Prime Nalgene™ pump sprayer (preferably about 50 times)

EXAMPLE 3

In this Example, the activity of a number of materials against Diisopropyl Fluorophosphate (DFP) was tested. DFP was chosen as a simulant for the nerve gas Sarin (GB) based on its analogous physical and chemical properties. Experimental studies have demonstrated that many materials with activity against DFP will also possess activity against Sarin, as well as other G agents and possibly VX. All materials were evaluated for their direct impact on DFP using Ellman's assay, See Ellman, G. L., Courtney, D., Andres, Jr., V., and Featherstone, R. M., *A New and Rapid Colorimetric Determination of Acetylcholinesterase Activity*, Biochemical Pharmacology, Vol. 7, pp. 88–95 (1960), and their ability to challenge DFP. In the Ellman's assay, demonstration of Bovine Serum Albumin (BSA) activity against DFP requires pre-incubation of BSA with DFP prior to the addition of the colorimetric substrate.

TABLE 1

DFP TESTING

| TEST CONDITION | RESULT |
| --- | --- |
| FFFP Foam Solution, no pre-incubation | No effect |
| FFFP Foam Solution, 5 min. pre-incubation | No effect |
| FFFP Foam Solution 10 min. pre-incubation | No effect |
| 3 mg/mL BSA, pH 7.5, buffered, no pre-incubation | No effect |
| 1 mg/mL BSA, pH 7.5, buffered, 5 min. pre-incubation | Minimal DFP inhibition observed |
| 2 mg/mL BSA, pH 7.5, buffered, 5 min. pre-incubation | Minimal DFP inhibition observed |
| 5 mg/mL BSA, pH 7.5, buffered, 5 min. pre-incubation | Minimal DFP inhibition observed |
| 10 mg/mL BSA, pH 7.5, buffered, 5 min. pre-incubation | Minimal DFP inhibition observed |
| 20 mg/mL BSA, pH 7.5, buffered, 5 min. pre-incubation | Minimal DFP inhibition observed |
| 30 mg/mL BSA, pH 7.5, buffered, 5 min. pre-incubation | Minimal DFP inhibition observed |
| 40 mg/mL BSA, pH 7.5, buffered, 5 min. pre-incubation | Minimal DFP inhibition observed |
| 5 mg/mL BSA, pH 7.5, buffered, 10 min. pre-incubation | Minimal DFP inhibition observed |
| 5 mg/mL BSA, pH 7.5, buffered, 15 min. pre-incubation | Minimal DFP inhibition observed |
| 3 mg/mL Collagenase, no pre-incubation | Minimal DFP inhibition observed |
| 1 mg/mL Collagenase, pH 7.5, buffered, 5 min. pre-incubation | Minimal DFP inhibition observed |
| 2 mg/mL Collagenase, pH 7.5, buffered, 5 min. pre-incubation | Minimal DFP inhibition observed |
| 3 mg/mL Collagenase, pH 7.5, buffered, 5 min. pre-incubation | Moderate DFP inhibition observed |
| 10 mg/mL Collagenase, pH 7.5, buffered, 5 min. pre-incubation | Moderate DFP inhibition observed |
| 20 mg/mL Collagenase, pH 7.5, buffered, 5 min. pre-incubation | Moderate DFP inhibition observed |
| 30 mg/mL Collagenase, pH 7.5, buffered, 5 min. pre-incubation | Moderate DFP inhibition observed |
| 10 mg/mL Collagenase, pH 7.5, buffered, 10 min. pre-incubation | Moderate DFP inhibition observed |
| 10 mg/mL Collagenase, pH 7.5, buffered, 15 min. pre-incubation | Moderate DFP inhibition observed |
| OPH-CLEC, 7.5 mg, 5 min. pre-incubation | >80% DFP inhibition observed |
| OPAA, 5 mg, 5 min. pre-incubation | >80% DFP inhibition observed |
| OPAA, 5 mg, 5 min. pre-incubation | >80% DFP inhibition observed |

As shown, a 5 minute pre-incubation allowed 1 mg/mL of BSA to slightly inhibit the effect of DFP. Also, it was shown that neither increased levels of BSA nor increased pre-incubation increased the activity of BSA against DFP. Direct inhibition of DFP was also observed for Collagenase. The activity of Collagenase was significantly higher than with BSA, and pre-incubation of the Collagenase was not required to observe an effect. By increasing the levels of Collagenase from 1 mg/mL to 3 mg/mL, increased activity against DFP was observed. However, further increase of Collagenase above 3 mg/mL did not show an increase in activity against DFP. Optimal activity using Collagenase was obtained at 3 mg/mL with a 5 minute pre-incubation period. Inhibition of DFP using OPH-CLEC (OPH-crosslinked enzyme crystals available from Altus, Inc., Cambridge, Mass.), and two preparations of OPAA were also demonstrated. It was further demonstrated the FFFP Foam Solution did not inhibit DFP.

EXAMPLE 4

A number of potential decontaminant enzymes were analyzed for their impact on acetylcholinesterase (AChE) using Ellman's assay. A primary concern in the development of a multi-enzyme based decontaminant composition is the possibility of an interaction between the active materials, resulting in the potential for self-inactivation. Direct competitive inhibition of agent binding to AChE would be expected to prevent action of the agent on humans. Concurrently, deactivation, and likely digestion, of the agent by digestive enzymes would result in extended activity, catalytic decontamination over time. Materials were tested in aqueous solutions.

TABLE 2

ELLMAN'S ACETYLCHOLINESTERASE ASSAY RESULTS

| TEST MATERIAL | ENZYME CONCENTRATION (3 mL total reaction volume) | SLOPE | COMMENTS |
|---|---|---|---|
| Silv-Ex ™ | 0% | 0.248 | No effect |
|  | 0.1% | 0.251 |  |
|  | 0.5% | 0.237 |  |
|  | 1.0% | 0.247 |  |
| Glucose Oxidase | 0 mg/mL | 0.251 | Concentration dependent interference With AchE |
|  | 0.225 mg/mL | 0.241 |  |
|  | 0.225 mg /mL (5 min pre-inc. w/AchE) | 0.223 |  |
|  | 0.45 mg/mL | 0.205 |  |
|  | 1.13 mg/mL | 0.118 |  |
| Lysozyme | 0 mg/mL | 0.260 | Concentration dependent interference with AchE |
|  | 3.3 mg/mL | 0.252 |  |
|  | 6.6 mg/mL | 0.231 |  |
|  | 16.7 mg mL | 0.193 |  |
| Lysing Enzyme | 0 mg/mL | 0.260 | Concentration dependent interference with AchE |
|  | 0.33 mg/mL | 0.239 |  |
|  | 0.66 mg/mL | 0.217 |  |
|  | 1.65 mg/mL | 0.167 |  |
| Protease (Pronase) | 0 mg/mL | 0.260 | Concentration dependent interference with AchE |
|  | 0.33 mg/mL | 0.240 |  |
|  | 1.65 mg/mL | 0.199 |  |
|  | 3.30 mg/mL | 0.168 |  |
| Chitinase | 0 mg/mL | 0.253 | No effect |
|  | 0.2 mg/mL | 0.266 |  |
|  | 0.4 mg/mL | 0.268 |  |
|  | 1.0 mg/mL | 0.276 |  |
| Lysostaphin | 0 units/mL | 0.253 | No effect |
|  | 58 units/mL | 0.342 |  |
|  | 116 units/mL | 0.279 |  |
|  | 292 units/mL | 0.273 |  |
| Mutanolysin | 0 units/mL | 0.253 | No effect |
|  | 360 units/mL | 0.265 |  |
|  | 720 units/mL | 0.267 |  |
|  | 2100 units/mL | 0.264 |  |
| Syntha CLEC-GO | ~0.23 mg/mL | 0.072 | Concentration dependent interference With AchE |
| Pepti-CLEC-TR | 3.3 mg/mL | 0.143 | Inconclusive |

EXAMPLE 5

A second concern in the use of enzymes is the potential impact of Silv-Ex™ surfactant on enzyme activity. Table 3 shows the effect of 0.1% aqueous Silv-Ex™, wherein 0.1% is the final concentration, on various enzymes.

TABLE 3

EFFECT OF 0.1% SILV-EX ™ AND DECONTAMINANT ENZYMES ON THE ELLMAN'S ACTEYLCHOLINESTERASE (AchE) ASSAY

| TEST MATERIAL | ENZYME CONCENTRATION | SLOPE | COMMENTS |
|---|---|---|---|
| AchE Control | N/A | 0.250 |  |
| Silv-Ex ™ Control | N/A | 0.235 | No significant effect observed |
| Glucose Oxidase | 0.225 mg/mL | 0.171 | Reduced activity observed |
| Lysozyme | 3.3 mg/mL | 0.133 | Precipitate formed. Reduced activity observed after settling |
| Lysing Enzyme | 0.33 mg/mL | 0.214–0.221 | No significant effect observed |
| Protease (Pronase) | 3.3 mg/mL | 0.133 | Precipitate formed. Reduced activity observed after settling |
| Chitinase | 0.2 mg/mL | 0.221 | No significant effect observed |
| Mutanolysin | 360 units/mL | 0.226 | No significant effect observed |
| Syntha CLEC-GO | ~0.23 mg/mL | 0.149 | Inconclusive due to precipitate suspension interference |

The tests demonstrate that Silv-Ex™ may potentially interfere with the activity of some enzymes. It was demonstrated that full activity was retained for chitanase, lysing enzyme and mutanolysin, while partial activity was retained for glucose oxidase, lysozyme, protease and synthaCLEC-GO. However, the results suggest that interference occurs mainly through reduction of enzyme activity by precipitation.

EXAMPLE 6

Direct microbiology challenge (i.e., no foam present) of materials on *Bacillus globigii* vegetative cells and spores was tested, with the results presented in Table 4.

Chemical treatment using urea has been shown to increase the susceptibility of spores to lysozyme (Gould et al., 1970) and, thus, was tested in combination with lysozyme in these studies. Chemical pre-treatment using EDTA (Ethylenediaminetetraacetic acid) has also been shown to alter the spore coat of a *Bacillus subtilis* strain and was, thus analyzed in combination with lysozyme for its potential effect on anthrax.

TABLE 4

MICROBIOLOGY TESTING USING *Bacillus globigii* VEGETATIVE CELLS AND SPORES IN TRYPTIC SOY BROTH (TSB)

| TEST ADDITION | RESULT (Cells) | RESULT (Spores) |
|---|---|---|
| THPS, 7500 ppm | Bacteriocidal | No spore germination observed |
| Benzalkonium chloride | Bacteriocidal to $10^8$ | No change observed |
| Triclosan 5000 ppm | Bacteriocidal | No spore germination observed |
| Chitinase | Modified morphology | No change observed |
| Lysozyme | No effect observed | No change observed |
| Mutanolysin | Bacteriocidal | Reduced spore germination |
| Streptomycin | No effect observed | Reduced spore germination |

TABLE 4-continued

MICROBIOLOGY TESTING USING *Bacillus globigii* VEGETATIVE CELLS AND SPORES IN TRYPTIC SOY BROTH (TSB)

| TEST ADDITION | RESULT (Cells) | RESULT (Spores) |
|---|---|---|
| Mutanolysin and Streptomycin | Bacteriocidal | Reduced spore germination |
| 1.7M Urea + Lysozyme | No effect observed | No spore germination observed |
| 1.7M Urea | No effect observed | Slight growth rate reduction |
| 270 mM EDTA + Lysozyme | 1.5 log growth rate reduction observed | No spore germination observed |
| 270 mM EDTA | No effect observed | No change observed |

EXAMPLE 7

The decontamination of spores using Silv-Ex™ foam was tested, and the results are set out below in Table 5.

TABLE 5

FOAM DECONTAMINANT TESTING USING *Bacillus globigii* SPORES ON TRYPTIC SOY AGAR PLATES

| TEST CONDITION | RESULT |
|---|---|
| FFFP foam spray | Induced sporulation. |
| 0.1% Silv-Ex™ foam spray | No effect. Normal germination observed. |
| 0.1% Silv-Ex™ foam + 2700 ppm triclosan | Germination inhibited. Spores non-viable. |

EXAMPLE 8

Biocide Blend Testing

The decontamination capabilities of various biocide blends against a variety of bacteria were tested while varying pH, Silv-Ex™ levels, and biocide mixture compositions. Organisms were prepared on Trypticase Soy Agar (TSA) plates and directly challenged against expanded foam prepared using individual biocide blends. The results are set out in Table 6.

TABLE 6

MICROBIAL CHALLENGE OF DECONTAMINANT BIOCIDE BLENDS ON TSA PLATES

| Components | Concentration | *Bactillus subtilis* var. *globigii* 51189 | *Bactillus subtilis* var. *globigii* 51189 spores | *Bactillus thuringiensis* 29730 bacteria | *Bacillus thuringiensis* 29730 spores | *Bacillus cereus* 49063 bacteria |
|---|---|---|---|---|---|---|
| Silv-Ex™ | 0.47% | N | N | N | N | N |
| BAC | 800 ppm | | | | | |
| THPS | 2.5% | | | | | |
| Triclosan | 1.9% | | | | | |
| pH | 7.02 | | | | | |
| Silv-Ex™ | 0.53% | N | N | N | N | N |
| BAC | 800 ppm | | | | | |
| THPS | 2.0% | | | | | |
| Triclosan | 1.2% | | | | | |
| pH | 7.14 | | | | | |
| Silv-Ex™ | 0.80% | N | S | N | N | N |
| BAC | 280 ppm | | | | | |
| THPS | 1.0% | | | | | |
| Triclosan | 0.8% | | | | | |
| pH | 7.03 | | | | | |
| Silv-Ex™ | 0.87% | N | N | N | N | N |
| BAC | 280 ppm | | | | | |
| THPS | 0.5% | | | | | |
| Triclosan | 0.5% | | | | | |
| pH | 2.32 | | | | | |
| Silv-Ex™ | 0.80% | N | N | N | N | N |
| BAC | 280 ppm | | | | | |
| THPS | 1.0% | | | | | |
| Triclosan | 0.5% | | | | | |
| pH | 2.16 | | | | | |
| Silv-Ex™ | 0.40% | N | N | N | N | N |
| BAC | 1120 ppm | | | | | |
| THPS | 2.5% | | | | | |
| Triclosan | 0.5% | | | | | |
| pH | 2.13 | | | | | |
| Silv-Ex™ | 0.80% | C | C | C | C | C |
| BAC | 280 ppm | | | | | |
| THPS | 1.0% | | | | | |
| Triclosan | 0.5% | | | | | |
| pH | 7.60 | | | | | |
| Silv-Ex™ | 0.80% | C | C | C | C | C |
| BAC | 280 ppm | | | | | |
| THPS | 1.0% | | | | | |
| Triclosan | 0.5% | | | | | |
| pH | 7.16 | | | | | |

TABLE 6-continued

MICROBIAL CHALLENGE OF DECONTAMINANT BIOCIDE BLENDS ON TSA PLATES

| Components | Concentration | Bactillus subtilis var. globigii 51189 | Bactillus subtilis var. globigii 51189 spores | Bactillus thuringiensis 29730 bacteria | Bacillus thuringiensis 29730 spores | Bacillus cereus 49063 bacteria |
|---|---|---|---|---|---|---|
| Collagenase | 0.3 mg/mL | | | | | |

"C" - Bacteriocidal;
"S" - Bacteriostatic;
"N" - No Effect

EXAMPLE 9

Individual colonies of *Bacillus globigii* vegetative cells and spores were placed onto membranes and tested using foams and supplemented foams to examine the impact of supplemented lysozyme on bacterial activity.

TABLE 7

MICROBIOLOGY TESTING USING *Bacillus globigii* SPORES ON MEMBRANES

| TEST CONDITION | RESULT |
|---|---|
| 0.1% Silv-Ex ™ foam spray | No effect Normal germination observed |
| 0.1% Silv-Ex ™ + Urea + Lysozyme | No spore germination observed. Appears bacteriocidal |
| 0.1% Silv-Ex ™ + EDTA + Lysozyme | No spore germination observed. Appears bacteriocidal |

The tests verified that Silv-Ex™ does not appear to negatively impact enzyme activity. Further, it was shown that no spore germination was observed by the addition of lysozyme.

EXAMPLE 10

The stability of the Silv-Ex™ foam concentrate and blend of biocides was tested at various temperatures, and the results are shown below.

TABLE 8

BIOCIDE PREPARATION STORAGE STABILITY TESTING

| TEMPERATURE | DURATION | RESULT | EXTRAPOLATED RT STABILITY |
|---|---|---|---|
| −20° C. | 48 hours | Stable | N/A |
| 4–6° C. | 2 months | Stable | N/A |
| Room Temperature | 3 months | Stable | 3 months |
| 60° C. | 4 weeks | Stable | 13 months |

EXAMPLE 11

Specific experimental protocols for testing the decontaminant compositions were developed based on similar efforts IITRI (Illinois Institute of Technology Research Institute) performed for Sandia National Laboratories (SNL).

The IITRI protocol allowed for the evaluation of 3 different biological pathogen decontaminant formulations. Blends with and without THPS were analyzed to provide alternative biocide blends. At temperatures above 160° C., THPS decomposes to form phosphine and oxides of phosphorous, making THPS less desirable for use in actual fire situations.

Results of these studies showed that a number of biocide blends that excluded THPS were capable of bacteriocidal activity against all BW surrogate organisms tested.

Results from the trials utilizing the preferred single strength formulation comprising approximately 0.5% triclosan, 0.5% BAC, 1.5% THPS, 1 mM manganese chloride, 7 mg/L OPAA enzyme, 0.1 mg/mL bovine serum albumin, 50 mM sodium phosphate buffer and 2.0% Silv-Ex™ indicate reduction of Anthrax spore levels from $7 \times 10^7$ cfu (colony forming units) to below detectable levels, achieving a greater than 7-log kill. The test results also show that the foam is active against Sarin and is able to eliminate greater than 99% of the Sarin present within 60 minutes.

EXAMPLE 12

Blended biocide solutions were prepared containing 1.0% Silv-Ex™, 5000 ppm triclosan, and varying ppm of THPS and BAC, adjusted to a pH ranging from 7.45 to 7.55. These solutions were used in direct microbial foam challenges against *Bacillus globigii* vegetative cells and spores, *Bacillus cereus* vegetative cells and *Bacillus thuringiensis* vegetative cells and spores that had been coated and dried onto glass slides as described in EXAMPLE 2. The results are set out in Table 9.

TABLE 9

BROAD MICROBIAL CHALLENGE OF DECONTAMINANT BIOCIDE BLENDS ON GLASS SLIDES

| | Concentration (final volume) 1.0% Silv-Ex ™ | Bacillus subtilis var. globigii 51189 bacteria | Bacillus subtilis var. globigii 51189 spores | Bacillus thuringiensis 29730 bacteria | Bacillus thuringiensis 29730 spores | Bacillus cereus 49063 bacteria |
|---|---|---|---|---|---|---|
| BAC | 240 ppm | S | S | S | S | N |
| THPS | 4875 ppm | | | | | |

TABLE 9-continued

BROAD MICROBIAL CHALLENGE OF DECONTAMINANT BIOCIDE BLENDS ON GLASS SLIDES

| | Concentration (final volume) 1.0% Silv-Ex ™ | Bacillus subtilis var. globigii 51189 bacteria | Bacillus subtilis var. globigii 51189 spores | Bacillus thuringiensis 29730 bacteria | Bacillus thuringiensis 29730 spores | Bacillus cereus 49063 bacteria |
|---|---|---|---|---|---|---|
| Triclosan pH 7.50 | 5000 ppm | | | | | |
| BAC | 60 ppm | S | S | C | S | N |
| THPS | 9750 ppm | | | | | |
| Triclosan pH 7.45 | 5000 ppm | | | | | |
| BAC | 240 ppm | C | C | C | C | S |
| THPS | 9750 ppm | | | | | |
| Triclosan pH 7.55 | 5000 ppm | | | | | |
| BAC | 240 ppm | S | N | S | S | N |
| THPS | none | | | | | |
| Triclosan pH 7.50 | 5000 ppm | | | | | |

"C" - Bacteriocidal;
"S" - Bacteriostatic;
"N" - No Effect

EXAMPLE 13

Additional testing was performed to determine the efficacy of the formulation against the following targets using the following test procedures:

A. *Escherichia coli* O157:H7 (American Type Culture Collection (ATCC) 43895)—Bacteria First Trial Run Slide treatments (taken at 15, 30, and 60 minutes): Glass slides were soaked separately each with about 10,000,000 cfu of *E. coli* O157:H7. The slides were allowed to dry for 24 hours at a relative humidity of 34% at 24° C. and biocide solutions (about 2.0 mL) were then applied as even foamy films. The slides were swabbed after biocide application drying—under a bio-hood. Nutrient agar plates were swabbed for growth determination after 24–48 hours. The run-off of foam from treatment was also plated for the presence of viable organisms present in the foam.

Preliminary Results

Growth was not detected on agar plates or in the residual foam after 48 hours of incubation. The solution was effective and completely bactericidal at 15 minutes.

Final Set-up and Testing

1. The bacteria were grown in nutrient broth to an optical density yielding $10^9$ cfu/mL organisms.
2. Deposit 100 μL of the suspension on triplicate frosted glass slides (25×75 mm) and air dry under aseptic conditions for 24 hours (Humidity: 34%).
3. Place slides in separate 1000 mL glass beakers.
4. Spray 100 mL of foam in a separate glass beaker and pour over each separate slide.
5. After each exposure period, remove slides and place in sterile water with a stir bar for two hours.
6. Collect the foam for organism viability testing.
7. Plate from the foam and slide wash (100 μL) onto nutrient agar plates at $10^0$–$10^{-5}$ serial dilutions and incubate for three days at 37° C.
8. Count the plates and compare with control numbers.

B. *Salmonella cholerasuis* (*Enteritidis*) (ATCC 49214)—Bacteria

First Trial Run

Slide treatments (taken at 15, 30, and 60 minutes): Glass slides were soaked separately each with about 10,000,000 cfu of *Salmonella cholerasuis*. The slides were allowed to dry for 24 hours (Temp: 24° C.; Relative humidity: 34%). Biocide solutions (about 2.0 mL) were then applied as even foamy films and allowed to dry in a biosafety cabinet. The dried slides were swabbed for growth determination on nutrient agar plates after 24–48 hours. The run-off of foam from treatment was also plated for the presence of viable organisms present in the foam.

Preliminary Results

Growth was not detected on agar plates or in the residual foam after 48 hours of incubation. The solution was effective and completely bactericidal at 15 minutes.

Final Set-up and Testing

1. The bacteria were grown in nutrient broth to an optical density yielding $10^9$ cfu/mL organisms.
2. Deposit 100 μL of the suspension on triplicate frosted glass slides (25×75 mm) and air dry under aseptic conditions for 24 hours (Humidity: 34%).
3 Place slides in separate 1000 mL glass beakers.
4. Spray 100 mL of foam in a separate glass beaker and pour over each separate slide.
5. After each exposure period, remove slides and place in sterile water with a stir bar for two hours.
6. Collect the foam for organism viability testing.
7. Plate from the foam and slide wash (100 μL) onto nutrient agar plates at $10^0$–$10^{-5}$ serial dilutions and incubate for three days at 37° C.
8. Count the plates and compare with control numbers.

C. *Bacillus cereus* Bacteriophage (ATCC 12826-B1)—Bacterial Virus

First Trial Run

*Bacillus cereus* phage was recovered from a nutrient agar plate (about 0.4° C.). This phage is lytic against its host (*Bacillus cereus*, ATCC 12826). An aliquot (100 μL of a 1.0 mg/mL nutrient broth solution) was used to initiate bacteriophage growth in broth (10 mL) containing the host. The bacteriophage was allowed to grow for 19 hours at 30° C. in a water bath. After incubation, the broth was spun down and treated with chloroform to eliminate the residual live bacteria from the bacteriophage-containing solution. The supernatant was then collected and an aliquot tested against a plated host to determine active phage titer. One mL of the bacteriophage solution was placed on a slide and dried overnight (Temp: 24° C.; Relative humidity: 34%). One mL of foamy biocide was placed on the slide and allowed to dry for various time periods (15, 30, and 60 minutes). After exposure, the slides were rinsed with distilled water and a thin layer (0.5 mL) of top agar containing the host bacteria was plated on the slide top to count any active phage that could remain. Control testing was also performed and results compared.

Final Set-up and Testing

The final test protocol was unchanged from initial testing.

D. *Staphylococcus aureus*—α-hemolysin (Obtained from Sigma)—Toxin

First Trial Run

Toxin [0.1 mg protein] was suspended in 1 mL of nutrient broth. A small aliquot (10 μL) of toxin was challenged with varying quantities of biocide (10 μL, 100 μL, 1 mL, and 5 mL) at two incubation temperatures (4° C. and 37° C.). Upon mixing, the toxin:foam mixtures were then incubated for various time periods (15, 30, 60, and 300 minutes). After incubation, 10 μL aliquots were removed, placed on rabbit blood cells, and tested for lytic activity (37° C. for 30 minutes, 4° C. for 30 minutes. Qualitative results were determined by visual assessment of hemolysis of the rabbit blood cells within the agar (visible as clear regions).

Preliminary Results

Most effective quantity was 5 mL of biocide against 10 μL of toxin.

Final Set-up and Testing

The final test protocol was unchanged from initial testing.

E. *Aspergillus niger* (ATCC 16404)—Fungal Spores

First Trial Run

Slide treatments (taken at 15, 30, and 60 minutes): Glass slides were soaked separately each with about 100,000 spores of *Aspergillus niger*. The fungi were allowed to sporulate after plating on Sabouraud agar. Spores grew after 8 days and various warm/cold incubation change treatments. Spores were collected using scotch tape, suspended in sterile water, filtered for enumeration, and then resuspended in sterile water. Collected fungal spores were placed on slides and allowed to dry for 24 hours at a relative humidity of 34% at 24° C. and biocide solutions (about 2.0 mL) were then applied as even foamy films. The slides were swabbed after exposure periods of biocide application drying—under a bio-hood. Sabouraud agar plates were swabbed for determination of growth after 24 to 96 hours. The foam run-off after treatment was also plated for the presence of viable spores that might be present in the foam.

Preliminary Results

Growth was not detected on either agar plates or in the residual foam after 48 hours of incubation. The solution appeared effective and completely fungicidal at 30 minutes.

Final Set-up and Testing

1. Aspergillus spores were washed and suspended in sterile de-ionized water (approximate concentration: $5.6 \times 10^5$ spores/mL).
2. Deposit 100,000 spores in water on triplicate frosted glass slides (25×75 mm) and air dry under aseptic conditions for 24 hours (Temp: 24° C.; Relative humidity: 34%). Place slides in separate 1000 mL glass beakers.
3. Place 100 mL foam in separate glass beaker and pour over each separate slide.
4. After exposure, remove slides and place in sterile water with a stir bar for two hours.
5. Collect the foam for spore viability testing.
6. Plate the spores from the foam and slide wash (200 μL) onto Sabouraud agar plates at $10^0$–$10^2$ serial dilutions and incubate for seven days at 35 to 37° C.
7. Count the plates and compare with control numbers.

F. *Giardia intestinalis* (ATCC 30957)—Protozoa/Parasite

First Trial Run

Slide treatments (taken at 15, 30, and 60 minutes): Glass slides were soaked separately each with about 3000 cysts of *Giardia intestinalis*. The parasite was allowed to form cysts over two weeks after various growth requirements were adjusted to optimize growth conditions. The cysts were suspended in nutrient broth and quantified by optical microscopy. Collected cysts were placed on slides and allowed to dry for 24 hours (Temp: 24° C.; Relative humidity: 34%). Biocide solutions (about 2.0 mL) were then applied as even foamy films. The slides were rinsed gently and swabbed for viable cysts. The swabs were placed in nutrient broth for growth determination after 24 to 96 hours.

Preliminary Results

Based on both optical microscopy and overall changes in turbidity, application of the foam appeared slightly effective in eliminating *Giardia* cysts at 30 minutes with improved activity seen after 60 minutes exposure Final Set-up and Testing 1. Cysts were suspended in sterile de-ionized water (approximate concentration: $3 \times 10^3$ spores/mL).
2. Deposit cysts in water on triplicate frosted glass slides (25×75 mm) and air dry under aseptic conditions for 24 hours—humidity 34%.
3. Place slides in separate 1000 mL glass beakers.
4. Place 100 mL foam in separate glass beaker and pour over each separate slide.
5. After an exposure period, remove slides and place in sterile water with a stir bar for two hours.
6. Collect the foam for cyst viability testing. Take an aliquot from the wash and place in nutrient agar for cyst activation. Verify cyst activity results by optical microscopy.

The formulation was effective against these other biological materials in tests of both the complete decontaminant foam formulation (including Sarin hydrolyzing enzyme) and the biocidal component alone. A summary of results is presented in Table 10.

TABLE 10

SUMMARY OF SLIDE TESTING

| Biological Tested | Quantity tested | Biocide challenge amount | Foam Activity | | |
|---|---|---|---|---|---|
| | | | 5 min | 30 min | 1 hour |
| *E. coli* O157:H7 | $2.3 \times 10^8$ cfu | 100 mL | E | E | E |
| Salmonella spp. | $3.1 \times 10^8$ cfu | 100 mL | E | E | E |
| *B. cereus* bacteriophage | 73 pfu | 100 mL | NE | E | E |

TABLE 10-continued

SUMMARY OF SLIDE TESTING

| Biological Tested | Quantity tested | Biocide challenge amount | Foam Activity | | |
|---|---|---|---|---|---|
| | | | 5 min | 30 min | 1 hour |
| Staphylococcus aureus - α-hemolysin | 1.0 μg | 5 mL | NE | NE | E (>4 hr) |
| Aspergillus niger | 1 × 10$^5$ spores | 100 mL | PE | E | E |
| Giardia spp. Cysts | ~1 × 10$^3$ cysts | 100 mL | NE | PE | E |

Biocide: 100 mL w/17 μL OPAA (unless otherwise stated)
E - (Effective) Biological activity eliminated
PE - (Partially Effective) Significant reduction in biological activity
NE - (Not Effective) biological activity unaffected Based on testing against a variety of biological materials, it was shown that the decontaminant composition is effective against a broad spectrum of potential biological threats.

As demonstrated, the decontaminant composition is effective against vegetative cells and specific efficacy has been demonstrated against two prominent food-borne pathogens, *E. coli* O157:H7 and *Salmonella cholerasuis* within 15 minutes of application.

As demonstrated using *B. cereus* bacteriophage as a model system for viruses, the decontaminant composition is effective against viruses within 30 minutes of application.

The decontaminant composition is effective against fungi and specific efficacy has been demonstrated against the common fungi, *Aspergillus niger*, within 30 minutes of application.

The decontaminant composition is effective against parasitic organisms, as demonstrated using *Giardia* cysts. The decontaminant composition was effective against *Giardia* cysts within 60 minutes of application. This water-borne pathogen is recognized to be particularly resistant to traditional decontamination using UV light.

The decontaminant composition shows some effect against biological toxins as demonstrated by the reduction in toxin activity against *Staphylococcus aureus*—α-hemolysin after at least 4 hours of exposure.

Although preferred embodiments of the invention have been described using specific terms, such description is for illustrative purposes only, and it is to be understood that changes and variations may be made without departing from the spirit or scope of the following claims.

What is claimed:

1. A chemical agent and biological pathogen decontamination composition comprising effective amounts of:
   a biocide blend of triclosan, tetrakishydroxymethyl phosphonium sulfate and benzalkonium chloride; and
   an OPAA enzyme.

2. A composition of claim 1, further comprising a foam forming material.

3. The composition of claim 2, wherein the foam forming material is a fire fighting foam.

4. The composition of claim 3, wherein the fire fighting foam is present from about 1.5 to 3 wt %.

5. The composition of claim 1 further comprising at least one chemical agent binding protein.

6. The composition of claim 5, wherein the at least one chemical agent binding protein is bovine serum albumin.

7. The composition of claim 1 further containing a phosphate buffer.

8. The composition of claim 1 further containing trace amounts of manganese chloride.

* * * * *